United States Patent
Umetani et al.

(10) Patent No.: US 9,150,538 B2
(45) Date of Patent: Oct. 6, 2015

(54) METHOD FOR PRODUCING 4, 4-DIFLUORO-3,4-DIHYDROISOQUINOLINE DERIVATIVES

(71) Applicant: MITSUI CHEMICALS AGRO, INC., Minato-ku (JP)

(72) Inventors: Hideki Umetani, Yasu (JP); Nobuhiro Kondo, Mobara (JP); Fumie Kajino, Yasu (JP)

(73) Assignee: MITSUI CHEMICALS AGRO, INC., Tokyo (JP)

( * ) Notice: Subject to any disclaimer, the term of this patent is extended or adjusted under 35 U.S.C. 154(b) by 0 days.

(21) Appl. No.: 14/347,468

(22) PCT Filed: Sep. 28, 2012

(86) PCT No.: PCT/JP2012/075084
§ 371 (c)(1),
(2) Date: Mar. 26, 2014

(87) PCT Pub. No.: WO2013/047749
PCT Pub. Date: Apr. 4, 2013

(65) Prior Publication Data
US 2014/0235862 A1 Aug. 21, 2014

(30) Foreign Application Priority Data
Sep. 29, 2011 (JP) ................. 2011-213687

(51) Int. Cl.
C07D 217/02 (2006.01)
C07D 215/00 (2006.01)
C07D 401/04 (2006.01)
A01N 43/42 (2006.01)

(52) U.S. Cl.
CPC .............. *C07D 401/04* (2013.01); *A01N 43/42* (2013.01)

(58) Field of Classification Search
CPC .................................... C07D 401/04
USPC .................................. 546/144, 164
See application file for complete search history.

(56) References Cited

U.S. PATENT DOCUMENTS

| | | | |
|---|---|---|---|
| 2008/0275242 A1 | 11/2008 | Ito et al. | |
| 2012/0282349 A1 | 11/2012 | Tamagawa et al. | |

FOREIGN PATENT DOCUMENTS

| | | | |
|---|---|---|---|
| WO | WO 2005/070917 A1 | 8/2005 | |
| WO | WO 2007/011022 A1 | 1/2007 | |
| WO | WO 2011/077514 A1 | 6/2011 | |

OTHER PUBLICATIONS

Yoneda, 1991, Tetrahedron, 1991, 47(29), 5329-5365.*
Dorwald F. A. Side Reactions in Organic Synthesis, 2005, Wiley: VCH, Weinheim p. IX of Preface p. 1-15.*
International Search Report (PCT/ISA/210) mailed on Nov. 13, 2012, by the Japanese Patent Office as the International Searching Authority for International Application No. PCT/JP2012/075084.
Jikken Kagaku Koza 19 Yuki Gosei I—Tanka Suiso Halogen Kagobutsu-, 4th edition, 1992, pp. 378-384.
Ishikawa et al., Fusso no Kagobutsu—sono Kagaku to Oyo, 1st edition, 1979, pp. 80-82.
Haufe, "Triethylamine Trishydrofluoride in Synthesis", Journal fuer Praktische Chemie / Chemiker-Zeitung, 1996, pp. 99-113.
Dai et al., "Advances in the Application of Triethylamine Tris(hydrofluoride) to Organic Synthesis", Chinese Journal of Organic Chemistry, 2009, pp. 1307-1316, vol. 29, No. 9.
International Preliminary Report on Patentability (Form PCT/IB/373) and the Written Opinion of the International Searching Authority (Form PCT/ISA/237) issued on Apr. 1, 2014, in the corresponding International Application No. PCT/JP2012/075084. (6 pages).
Middleton, "New Fluorinating Reagents. Dialkylaminosulfur Fluorides", Journal of Organic Chemistry, (1975), vol. 40, No. 5, pp. 574-578.

* cited by examiner

*Primary Examiner* — Nizal Chandrakumar
(74) *Attorney, Agent, or Firm* — Buchanan, Ingersoll & Rooney PC

(57) ABSTRACT

Provided is a simple and efficient method for the large-scale production of a 4,4-difluoro-3,4-dihydroisoquinoline derivative. In the method for producing a 4,4-difluoro-3,4-dihydroisoquinoline derivative represented by general formula (1):

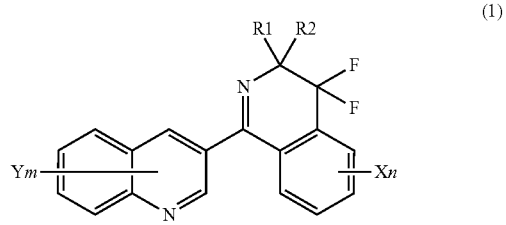

a compound represented by general formula (2):

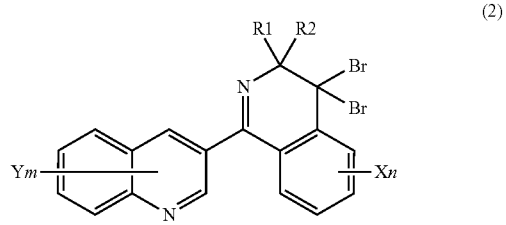

is reacted with hydrogen fluoride.

4 Claims, No Drawings

METHOD FOR PRODUCING 4,4-DIFLUORO-3,4-DIHYDROISOQUINOLINE DERIVATIVES

TECHNICAL FIELD

The present invention relates to a method for producing a 4,4-difluoro-3,4-dihydroisoquinoline derivative.

BACKGROUND ART

Numerous chemicals have been proposed for the purpose of controlling diseases in agricultural and horticultural crops. For example, Patent Document 1 and Patent Document 2 disclose chemicals containing a 4,4-difluoro-3,4-dihydroisoquinoline derivative represented by general formula (1):

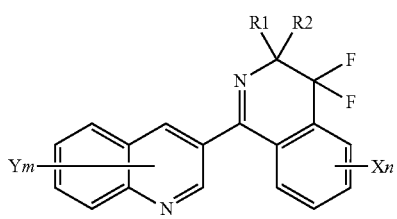

(1)

However, a specific method for preparing the aforementioned 4,4-difluoro-3,4-dihydroisoquinoline derivative represented by general formula (1) is not described in the aforementioned patent documents. When producing this group of compounds, an efficient method comprises deoxyfluorinating the ketone group of an isoquinolin-4(3H)-one derivative represented by general formula (4) disclosed in Patent Document 1:

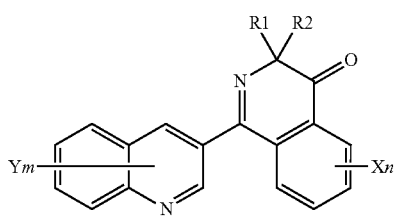

(4)

With the foregoing background, there has been a fervent desire for the development of a production method that enables 4,4-difluoro-3,4-dihydroisoquinoline derivatives to be synthesized easily and allows them to be produced on an industrial scale.

PRIOR ART DOCUMENTS

Patent Documents

Patent Document 1: International Publication No. WO 2005/70917
Patent Document 2: International Publication No. WO 2011/77514

Non-Patent Documents

Non-Patent Document 1: Journal of Organic Chemistry, Vol. 40, pp. 574-578 (1975)

DISCLOSURE OF THE INVENTION

Problems to be Solved by the Invention

An object of the present invention is to provide a simple and efficient method for producing a 4,4-difluoro-3,4-dihydroisoquinoline derivative.

Means for Solving the Problems

As a result of conducting extensive studies to solve the aforementioned problems, it was found that a target 4,4-difluoro-3,4-dihydroisoquinoline derivative can be produced after reacting a 3,4-dihydroisoquinoline derivative and a brominating agent to convert to a 4,4-dibromo-3,4-dihydroisoquinoline derivative, by reacting the 4,4-dibromo-3,4-dihydroisoquinoline derivative with hydrogen fluoride. This method makes it possible to supply 4,4-difluoro-3,4-dihydroisoquinoline derivatives both easily and efficiently, thereby leading to completion of the present invention.

Namely, the present invention is:

[1] a method for producing a compound represented by general formula (1):

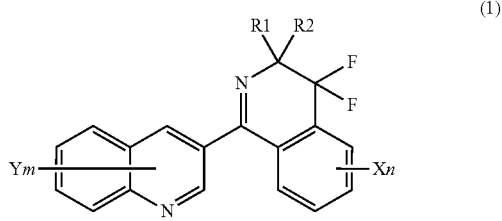

(1)

wherein R1 and R2 independently represent an optionally substituted alkyl group having 1 to 6 carbon atoms or R1 and R2 together with the carbon atom to which they are bound form an optionally substituted cycloalkyl group having 3 to 10 carbon atoms, X represents a halogen atom, optionally substituted alkyl group having 1 to 6 carbon atoms or optionally substituted alkoxy group having 1 to 6 carbon atoms, n represents an integer of 0 to 4, Y represents a halogen atom, optionally substituted alkyl group having 1 to 6 carbon atoms or optionally substituted alkoxy group having 1 to 6 carbon atoms, and m represents an integer of 0 to 6, comprising reacting a compound represented by general formula (2):

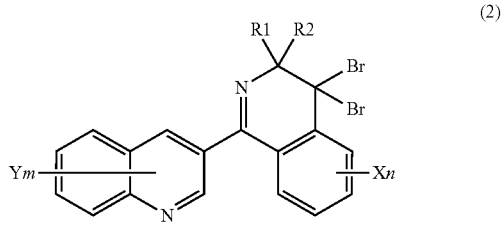

(2)

wherein R1, R2, X, Y, n and m are the same as previously defined, with hydrogen fluoride;

[2] the method for producing a compound represented by general formula (1) described in [1], wherein the compound represented by general formula (2) is obtained by reacting a compound represented by general formula (3):

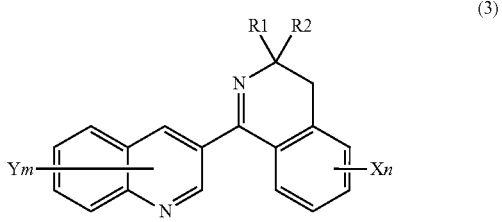

(3)

Effects of the Invention

According to the present invention, a method for producing a large amount of 4,4-difluoro-3,4-dihydroisoquinoline derivative can be provided. In addition, the method of the present invention is suitable for an industrial manufacturing method since the target compound can be prepared efficiently by simple operation.

MODE FOR CARRYING OUT THE INVENTION

The following provides a detailed explanation of embodiments for carrying out the present invention.

An explanation of general formula (1) is first provided.

R1 and R2 in general formula (1) are independent and may be the same or different.

The substituents of the optionally substituted alkyl group having 1 to 6 carbon atoms at R1 and R2 in general formula (1) refer to halogen atoms and alkoxy groups having 1 to 6 carbon atoms. The halogen atom is fluorine, chlorine, bromine or iodine. The alkoxy group having 1 to 6 carbon atoms represents a linear or branched alkoxy group, such as a methoxy group, ethoxy group, propoxy group, isopropoxy group, butyloxy group, isobutyloxy group, s-butyloxy group, t-butyloxy group, pentoxy group, isopentoxy group, 2-methylbutyloxy group, neopentoxy group, 1-ethylpropoxy group, hexyloxy group, 4-methylpentoxy group, 3-methylpentoxy group, 2-methylpentoxy group, 1-methylpentoxy group, 3,3-dimethylbutyloxy group, 2,2-dimethylbutyloxy group, 1,1-dimethylbutyloxy group, 1,2-dimethylbutyloxy group, 1,3-dimethylbutyloxy group, 2,3-dimethylbutyloxy group or 2-ethylbutyloxy group. It is preferably an alkoxy group having 1 to 4 carbon atoms and more preferably a methoxy group, ethoxy group, propoxy group or isopropoxy group. There are no particular limitations on the number of substituents and each substituent may be the same or different.

The alkyl group in the optionally substituted alkyl group having 1 to 6 carbon atoms at R1 and R2 in general formula (1) represents a linear or branched alkyl group, such as a methyl group, ethyl group, propyl group, isopropyl group, butyl group, isobutyl group, s-butyl group, t-butyl group, pentyl group, isopentyl group, 2-methylbutyl group, neopentyl group, 1-ethylpropyl group, hexyl group, 4-methylpentyl group, 3-methylpentyl group, 2-methylpentyl group, 1-methylpentyl group, 3,3-dimethylbutyl group, 2,2-dimethylbutyl group, 1,1-dimethylbutyl group, 1,2-dimethylbutyl group, 1,3-dimethylbutyl group, 2,3-dimethylbutyl group or 2-ethylbutyl group. It is preferably an alkyl group having 1 to 3 carbon atoms and more preferably a methyl group or ethyl group.

The substituents of the optionally substituted cycloalkyl group having 3 to 10 carbon atoms formed by R1 and R2 together with the carbon atom to which they are bound in general formula (1) have the same meaning as the substituents of the optionally substituted alkyl group having 1 to 6 carbon atoms at R1 and R2 in general formula (1). There are no particular limitations on the number of substituents and each substituent may be the same or different.

The cycloalkyl group in the optionally substituted cycloalkyl group having 3 to 10 carbon atoms formed by R1 and R2 together with the carbon atom to which they are bound in general formula (1) refers to monocyclic or polycyclic cycloalkyl group having 3 to 10 carbon atoms, such as a cyclobutyl group, cyclopentyl group, cyclohexyl group, cycloheptyl group or norbornyl group. It is preferably a cyclobutyl group, cyclopentyl group, cyclohexyl group or cycloheptyl group, and more preferably a cyclopentyl group.

The halogen atom at X in general formula (1) refers to fluorine, chlorine, bromine or iodine.

The optionally substituted alkyl group having 1 to 6 carbon atoms at X in general formula (1) has the same meaning as the optionally substituted alkyl group having 1 to 6 carbon atoms at R1 and R2 in general formula (1).

The substituents of the optionally substituted alkoxy group having 1 to 6 carbon atoms at X in general formula (1) refer to a halogen atom, that is, fluorine, chlorine, bromine or iodine. There are no particular limitations on the number of substituents and each substituent may be the same or different.

The alkoxy group of the optionally substituted alkoxy group having 1 to 6 carbon atoms at X in general formula (1) refers to a linear or branched alkoxy group, such as a methoxy group, ethoxy group, propoxy group, isopropoxy group, butyloxy group, isobutyloxy group, s-butyloxy group, t-butyloxy group, pentoxy group, isopentoxy group, 2-methylbutyloxy group, neopentoxy group, 1-ethylpropoxy group, hexyloxy group, 4-methylpentoxy group, 3-methylpentoxy group, 2-methylpentoxy group, 1-methylpentoxy group, 3,3-dimethylbutyloxy group, 2,2-dimethylbutyloxy group, 1,1-dimethylbutyloxy group, 1,2-dimethylbutyloxy group, 1,3-dimethylbutyloxy group, 2,3-dimethylbutyloxy group or 2-ethylbutyloxy group. It is preferably an alkoxy group having 1 to 4 carbon atoms and more preferably a methoxy group, ethoxy group, propoxy group or isopropoxy group.

n in general formula (1) is an integer of 0 to 4.

X may be the same or different when n in general formula (1) is 2 or more.

The halogen atom at Y in general formula (1) has the same meaning as the halogen atom at X in general formula (1).

The optionally substituted alkyl group having 1 to 6 carbon atoms at Y in general formula (1) has the same meaning as the optionally substituted alkyl group having 1 to 6 carbon atoms at X in general formula (1).

The optionally substituted alkoxy group having 1 to 6 carbon atoms at Y in general formula (1) has the same meaning as the optionally substituted alkoxy group having 1 to 6 carbon atoms at X in general formula (1).

m in general formula (1) is an integer of 0 to 6.

Y may be the same or different when m in general formula (1) is 2 or more.

R1, R2, X, Y, n and m in general formula (2) have the same meanings as in general formula (1).

The following provides an explanation of a method for converting from a compound represented by general formula (2) to a compound represented by general formula (1).

The hydrogen fluoride used in the reaction may be hydrogen fluoride alone or a reagent that is stabilized by hydrogen bonding, such as triethylamine trihydrofluoride, pyridine hydrofluoride or 1,3-dimethyl-2-imidazolidinone hydrofluoride. There are no particular limitations on the form of the reagent provided the reagent contains hydrogen fluoride and allows the target reaction to proceed.

Although there are no particular limitations on the amount of hydrogen fluoride used provided it is more than 2 equivalents based on the compound represented by general formula (2), it is preferably 2 equivalents to 20 equivalents from the viewpoint of economy.

A solvent can be used during the reaction. Although there are no particular limitations on the solvent provided it allows the reaction to proceed, examples of solvents that can be used include benzene-based solvents such as toluene, xylene, benzene, chlorobenzene or dichlorobenzene, nitrile-based solvents such as acetonitrile, ester-based solvents such as ethyl acetate, isopropyl acetate or butyl acetate, amide-based solvents such as N-methylpyrrolidone, N,N-dimethylformamide or N,N-dimethylacetamide, urea-based solvents such as 1,3-dimethyl-2-imidazolidinone, basic solvents such as pyridine, collidine, triethylamine or tributylamine, ether-based solvents such as tetrahydrofuran, diethyl ether, diisopropyl ether or methyl t-butyl ether, chlorine-based solvents such as dichloromethane, dichloroethane, chloroform or carbon tetrachloride, and hydrocarbon-based solvents such as hexane, heptane, cyclohexane or methylcyclohexane. In addition, these solvents can be used alone, or two or more types can be mixed at an arbitrary ratio.

Although there are no particular limitations on the amount of solvent used provided it allows the reaction to proceed, it is preferably 2 times to 30 times the weight of the compound represented by general formula (2) from the viewpoint of economy.

Although there are no particular limitations on the reaction temperature provided it allows the reaction to proceed, it is higher than 30° C. and lower than 120° C. or the boiling point of the solvent. The reaction temperature can be suitably set according to the reaction states.

Method for post-treatment of reaction can consist of mixing the reaction mixture with an aqueous alkaline solution obtained by dissolving potassium hydroxide, sodium hydroxide, sodium carbonate, potassium carbonate, sodium bicarbonate or potassium bicarbonate followed by a liquid separation procedure. At this time, a solvent that is incompatible with water can be added as necessary, examples of which include benzene-based solvents such as toluene, xylene, benzene, chlorobenzene or dichlorobenzene, ester-based solvents such as ethyl acetate, isopropyl acetate or butyl acetate, ether-based solvents such as diethyl ether, diisopropyl ether or methyl t-butyl ether, chlorine-based solvents such as dichloromethane, dichloroethane or chloroform, and hydrocarbon-based solvents such as hexane, heptane, cyclohexane or methylcyclohexane. In addition, these solvents can be used alone, or two or more types can be mixed at an arbitrary ratio. There are no particular limitations on the number of liquid separation procedures, and liquid separation can be carried out corresponding to the target purity and yield.

Although the moisture in the aforementioned resulting reaction mixture containing compound (1) can be removed with a desiccant such as sodium sulfate or magnesium sulfate, this operation is not essential.

The aforementioned resulting reaction mixture containing compound (1) can be subjected to distillation under reduced pressure to remove the solvent provided the compound does not decompose.

The reaction mixture containing compound (1) obtained after distilling off the solvent can be purified by washing, re-precipitating or recrystallizing with a suitable solvent. Examples of solvents used include water, alcohol-based solvents such as methanol, ethanol or isopropyl alcohol, benzene-based solvents such as toluene, xylene, benzene, chlorobenzene or dichlorobenzene, ester-based solvents such as ethyl acetate, isopropyl acetate or butyl acetate, ether-based solvents such as diethyl ether, diisopropyl ether or methyl t-butyl ether, and hydrocarbon-based solvents such as hexane, heptane, cyclohexane or methylcyclohexane. At this time, one type of solvent can be used alone or two or more types mixed at an arbitrary ratio can be used. In addition, the reaction mixture can also be purified by column chromatography. Purification is suitably set according to the target purity.

Moreover, the reaction mixture containing compound (1) can also be isolated as a salt of a compound represented by general formula (1) such as a compound represented by general formula (4):

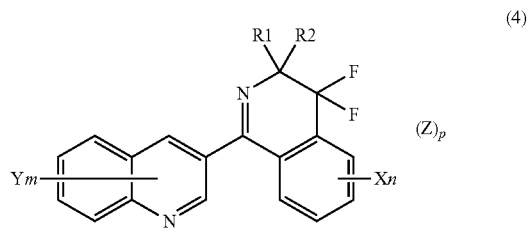

The acid at Z in general formula (4) refers to an inorganic acid such as hydrochloric acid, sulfuric acid or phosphoric acid, or an organic acid such as methanesulfonic acid, p-toluenesulfonic acid, oxalic acid or succinic acid.

The value of p in general formula (4) is 0.5 to 2.

A compound represented by general formula (4) can be prepared by adding a suitable solvent to the mixture containing a compound represented by general formula (1) followed by adding an acid.

Examples of the solvents added when preparing a compound represented by general formula (4) include water, alcohol-based solvents such as methanol, ethanol or isopropyl alcohol, benzene-based solvents such as toluene, xylene, benzene, chlorobenzene or dichlorobenzene, ether-based solvents such as tetrahydrofuran, diethyl ether, diisopropyl ether or methyl t-butyl ether, ester-based solvents such as ethyl acetate, isopropyl acetate or butyl acetate, and hydrocarbon-based solvents such as hexane, heptane, cyclohexane or methylcyclohexane. In addition, there are no particular limitations on the form in which solvents are used, and one type of solvent may be used alone or two or more types may be mixed at an arbitrary ratio.

Although there are no particular limitations on the amount of acid used when preparing a compound represented by general formula (4) provided the amount is more than 1 equivalent, the amount used is 1 equivalent to 15 equivalents from the viewpoint of economy.

The value of p of the resulting salt is 1 or 2 in the case of a monoacid, and the value of p of the resulting salt is 0.5 or 1 in the case of a diacid. There are no particular limitations on the form of the salt and it may be one salt alone or a mixture of a monoacid salt with a diacid salt.

A compound represented by general formula (4) can be washed, re-precipitated or recrystallized with a suitable solvent. Examples of solvents used include water, alcohol-based solvents such as methanol, ethanol or isopropyl alcohol, benzene-based solvents such as toluene, xylene, benzene, chlorobenzene or dichlorobenzene, ether-based solvents such as tetrahydrofuran, diethyl ether, diisopropyl ether or methyl t-butyl ether, ester-based solvents such as ethyl acetate, isopropyl acetate or butyl acetate, and hydrocarbon-based solvents such as hexane, heptane, cyclohexane or methylcyclohexane. There are no particular limitations on these solvents provided the target procedure can be carried out, and it may be one type of solvent alone or a mixed solvent of two or more types of solvents.

A compound represented by general formula (4) can be converted to a compound represented by general formula (1) by a basic substance. The basic substance refers to a substance such as potassium hydroxide, sodium hydroxide, sodium carbonate, potassium carbonate, sodium bicarbonate or potassium bicarbonate, and these can be used while dissolved in water. In addition, extraction can be carried out as necessary with a solvent that is incompatible with water, examples of which include benzene-based solvents such as toluene, xylene, benzene, chlorobenzene or dichlorobenzene, ester-based solvents such as ethyl acetate or butyl acetate, ether-based solvents such as diethyl ether, diisopropyl ether or methyl t-butyl ether, chlorine-based solvents such as dichloromethane, dichloroethane or chloroform, and hydrocarbon-based solvents such as hexane, heptane, cyclohexane or methylcyclohexane. There are no particular limitations on the number of liquid separation procedures, and the number thereof can be set as is suitable. The resulting compound represented by general formula (1) can be purified by washing, re-precipitation, recrystallization or column chromatography and the like using the same procedure as the aforementioned method for post-treatment of the reaction. Method for purification can be suitably set according to the target purity.

The following provides an explanation of a method for obtaining a compound represented by general formula (2).

R1, R2, X, Y, n and m in general formula (3) have the same meanings as in general formula (1).

Examples of brominating agents include 1,3-dibromo-5,5-dimethylhydantoin and N-bromosuccinimide.

A compound represented by general formula (3) can be prepared with reference to Patent Document 1.

When converting a compound represented by general formula (3) to a compound represented by general formula (2) with a brominating agent, a radical initiator such as a peracid or azo compound or light irradiation is required.

Although there are no particular limitations on the radical initiator provided the target bromination is allowed to proceed, a radical initiator having a 10-hour half-life temperature of lower than 90° C. is preferable.

Examples of the peracid as radical initiators include diisobutyryl peroxide, cumyl peroxyneodecanoate, di-n-propyl peroxydicarbonate, diisopropyl peroxydicarbonate, di-sec-butyl peroxydicarbonate, 1,1,3,3-tetramethylbutyl peroxyneodecanoate, di(4-t-butylcyclohexyl) peroxydicarbonate, di(2-ethylhexyl) peroxydicarbonate, t-hexyl peroxyneodecanoate, t-butyl peroxyneodecanoate, t-butyl peroxyneoheptanoate, t-hexyl peroxypivalate, t-butyl peroxypivalate, di(3,5,5,-trimethylhexanoyl) peroxide, dilauryl peroxide, 1,1,3,3-tetramethylbutyl peroxy-2-ethylhexanoate, disuccinic acid peroxide, 2,5-dimethyl-2,5-di(2-ethylhexanoylperoxy)hexane, t-hexyl peroxy-2-ethylhexanoate, di(4-methylbenzoyl) peroxide, t-butyl peroxy-2-ethylhexanoate, mixtures of di(3-methylbenzoyl) peroxide, benzoyl (3-methylbenzoyl) peroxide and dibenzoyl peroxide, dibenzoyl peroxide, 1,1-di(t-butylperoxy)-2-methylcyclohexane and 1,1-di(t-hexylperoxy)-3,3,5-trimethylcyclohexane.

Examples of the azo compound as radical initiators include 2,2'-azobis(isobutyronitrile), 2,2'-azobis(4-methoxy-2,4-dimethylvaleronitrile), 2,2'-azobis(2,4-dimethylvaleronitrile), dimethyl 2,2'-azobis(2-methylpropionate), There are no particular limitations on the amount of radical initiator used provided it allows the target reaction to proceed. The amount used is preferably 0.001 equivalents to 0.30 equivalents from the viewpoint of economy.

There are no particular limitations on the amount of brominating agent used provided it allows the target reaction to proceed, and it is more than 2 equivalents as bromine atoms. The amount used is preferably 2 equivalents to 4 equivalents as bromine atoms from the viewpoint of economy.

A solvent can be used when carrying out the reaction. Examples of the solvents include chlorine-based benzene solvents such as chlorobenzene or dichlorobenzene, halogen-based solvents such as carbon tetrachloride, hydrocarbon-based solvents such as hexane, heptane, cyclohexane or methylcyclohexane, and ester-based solvents such as ethyl acetate, isopropyl acetate or butyl acetate.

Although there are no particular limitations on the amount of solvent used in the reaction provided it allows the reaction to proceed, it is preferably 3 times the weight to 30 times the weight of the compound represented by general formula (3).

The reaction temperature can be set according to the type of radical initiator, and is higher than 30° C. and lower than 150° C. or the boiling point of the solvent.

As for a method for post-treatment of the reaction, by-products can be removed by carrying out a filtration procedure in the case that by-products formed from the brominating agent, such as 5,5-dimethylhydantoin in the case of 1,3-dibromo-5,5-dimethylhydantoin, have precipitated.

The reaction mixture of a compound represented by general formula (2) can be washed, re-precipitated or recrystallized with a suitable solvent. Examples of the solvents used at this time include benzene-based solvents such as toluene, xylene, benzene, chlorobenzene or dichlorobenzene, ester-based solvents such as ethyl acetate, isopropyl acetate or butyl acetate, ether-based solvents such as diethyl ether, diisopropyl ether or methyl t-butyl ether, chlorine-based solvents such as dichloromethane, dichloroethane or chloroform, and hydrocarbon-based solvents such as hexane, heptane, cyclohexane or methylcyclohexane. In addition, these solvents can be used alone or as a mixture of two or more types at an arbitrary ratio. In addition, the reaction mixture can also be purified by column chromatography. Purification can be suitably carried out according to the target purity.

A compound represented by general formula (2) obtained by reacting a compound represented by general formula (3) with a brominating agent can be converted to a compound represented by general formula (1) by reacting with hydrogen fluoride.

As a result, a 4,4-difluoro-3,4-dihydroisoquinoline derivative can be efficiently produced.

EXAMPLES

Although the following provides a more detailed description of the present invention by indicating examples thereof, the present invention is not limited to these examples. 3-(3,3-dimethyl-3,4-dihydroisoquinolin-1-yl)quinoline is referred to as Compound (I), 3-(4,4-dibromo-3,3-dimethyl-3,4-dihydroisoquinolin-1-yl) quinoline is referred to as Compound (II), 3-(4,4-difluoro-3,3-dimethyl-3,4-dihydroisoquinolin-1-yl) quinoline is referred to as Compound (III), 1,3-dibromo-5,5-dimethylhydantoin is referred to as DBH, and high-performance liquid chromatography is referred to as HPLC.

Comparative Example 1

Synthesis of Compound (III)

Using 3,3-dimethyl-1-(quinoline-3-yl)isoquinolin-4(3H)-one (referred to as Compound (IV)) as Substrate

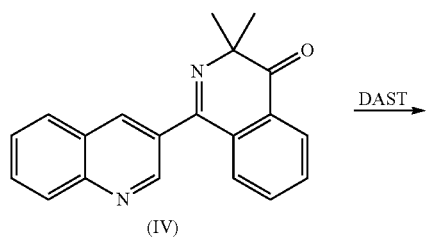

20 mL of (diethylamino)sulfur trifluoride were added to a mixture of 4.57 g of Compound (IV) and 5 mL of methylene chloride followed by heat refluxing for 13 hours. After cooling in air, the reaction mixture was treated with ice-cooled saturated aqueous sodium bicarbonate followed by extraction with methylene chloride. The resulting methylene chloride layer was washed with saturated brine solution and dried with magnesium sulfate followed by distilling off the solvent under reduced pressure and purifying the resulting residue by chromatography to obtain the target substance (1.42 g, yield: 28.9%). Raw material (2.89 g, recovery rate: 63.2%) was simultaneously recovered.

Example 1

Synthesis of Compound (II) by DBH

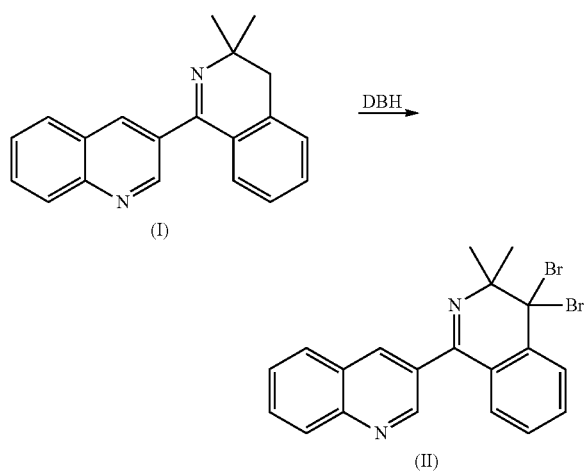

4.8 g of Compound (I) were dissolved in 48 ml of chlorobenzene followed by raising the temperature to 93° C. 2.64 g of DBH and 0.42 g of 2,2'-azobis(isobutyronitrile) (AIBN) were added and stirred for 5 minutes followed by again adding 2.64 g of DBH and 0.42 g of AIBN and stirring for 2 hours. After cooling to 15° C., the mixture was stirred for 1 hour and then filtered. After distilling the filtrate under reduced pressure to remove the solvent, 5 ml of a mixture of ethyl acetate and hexane (ethyl acetate:hexane=4:1) were added to the residue followed by stirring at 15° C., further adding 15 ml of hexane and stirring for 1 hour at the same temperature. The precipitate was then filtered out to obtain 6.68 g of Compound (II) as a pale yellow solid. The purity was 94.9%.

Material Data of Compound (II):
$^1$H-NMR (CDCl$_3$) δ: 9.13 (1H, d, J=2.0 Hz), 8.38 (1H, d, J=2.0 Hz), 8.21 (2H, t, J=8.1 Hz), 7.89 (1H, d, J=8.3 Hz), 7.82-7.78 (1H, m), 7.62 (2H, td, J=7.7, 4.1 Hz), 7.45-7.41 (1H, m), 7.24 (1H, d, J=7.3 Hz), 1.79 (6H, br s).

Example 2

Synthesis of Compound (III) Using Triethylamine Trihydrofluoride

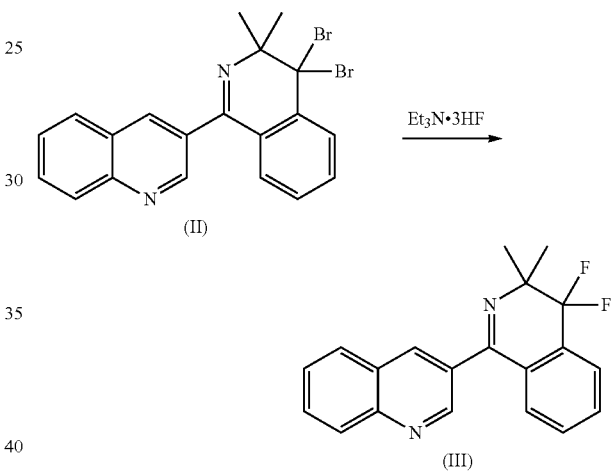

5.0 g of Compound (II) obtained in Example 1 and 5.73 g of triethylamine trihydrofluoride were added to 30 ml of xylene and allowed to react for 4 hours at 90° C. Next, 50 g of an 18% aqueous potassium hydroxide solution were dropped in while cooling with ice followed by stirring at room temperature. After separating the liquids of the resulting reaction mixture, the organic layer was concentrated under reduced pressure. 13 ml of methanol were added to the residue, and the resulting solution was added dropwise in 50% aqueous methanol solution. 26 ml of water were additionally added followed by stirring. The resulting precipitate was filtered out to obtain 3.33 g of the title compound as a pale yellow solid. The yield was 88%, thereby demonstrating the present method to be extremely superior to the method of Comparative Example 1. In addition, the $^1$H-NMR data of the resulting compound coincided with that described in Patent Document 1.

Example 3

Synthesis of Compound (III) Using Triethylamine Trihydrofluoride 1.47 g of triethylamine trihydrofluoride were added to 7.5 ml of acetonitrile followed by adding 1.21 g of Compound (II)

and allowing to react for 4 hours at 90° C. Measurement of the reaction mixture at this time by HPLC indicated that Compound (III) had formed in a reaction yield of 90%. After cooling to room temperature, the reaction mixture was added to an aqueous potassium hydroxide solution. Next, the resulting solution was extracted with ethyl acetate followed by drying with magnesium sulfate. After removing the magnesium sulfate, an aqueous methanol solution was added to the residue followed by stirring and filtering out the precipitate to obtain 0.67 g of Compound (III) as a pale yellow solid. Yield: 80%.

Example 4

Synthesis of Compound (III) Using Triethylamine Trihydrofluoride 0.85 g of triethylamine trihydrofluoride were added to 4 ml of toluene followed by adding 0.70 g of Compound (II) and allowing to react for 4 hours at 90° C. Measurement of the reaction mixture at this time by HPLC indicated that Compound (III) had formed in a reaction yield of 96%. After allowing to cool to room temperature, the reaction mixture was added to a 5% aqueous potassium hydroxide solution. After separating the liquids, the solvent was distilled off under reduced pressure. An aqueous methanol solution was added to the resulting residue and the precipitate was filtered out to obtain 0.43 g of Compound (III) as a pale yellow solid. Yield: 84%.

Example 5

Synthesis of Compound (III) Using Triethylamine Trihydrofluoride 0.80 g of triethylamine trihydrofluoride and 1.0 g of Compound (II) were added to 6 ml of heptane and allowed to react for 4 hours at 90° C. Measurement of the resulting reaction mixture by HPLC indicated that Compound (III) had formed in a reaction yield of 93%.

Example 6

Synthesis of Compound (III) Using Triethylamine Trihydrofluoride

The reaction was carried out in the same manner as in Example 5 with the exception of using butyl acetate instead of heptane. Measurement of the resulting reaction mixture by HPLC indicated that Compound (III) had formed in a reaction yield of 78%.

Example 7

Synthesis of Compound (III) Using Triethylamine Trihydrofluoride 0.88 g of triethylamine trihydrofluoride were added to 4 ml of triethylamine followed by adding 0.72 g of Compound (II) and allowing to react for 4 hours at 90° C.
Measurement of this reaction mixture by HPLC indicated that Compound (III) had formed in a reaction yield of 82%.

Example 8

Synthesis of Compound (III) Using 70% Pyridine Hydrofluoride 0.43 g of 70% pyridine hydrofluoride and 263 mg of pyridine were added to 6 ml of toluene followed by charging with 1.01 g of Compound (II). Next, the reaction mixture was stirred for 4 hours at 85° C. Analysis of the resulting reaction mixture by HPLC indicated that Compound (III) had formed in a reaction yield of 87%.

Example 9

Synthesis of Compound (II) by N-bromosuccinimide

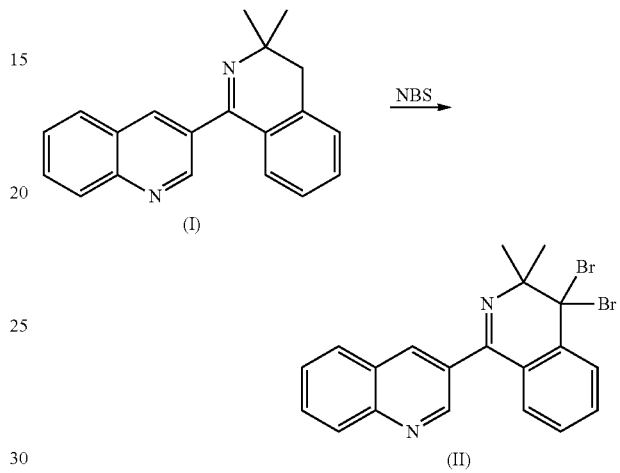

10 ml of chlorobenzene added with 1 g of Compound (I) were heated to 93° C. Next, 1.40 g of N-bromosuccinimide and 29 mg of AIBN were added and allowed to react for 2 hours at the same temperature. Measurement of the reaction mixture by HPLC indicated that Compound (II) had formed in a reaction yield of 90%.

Example 10

Synthesis of Compound (III) from Compound (I)

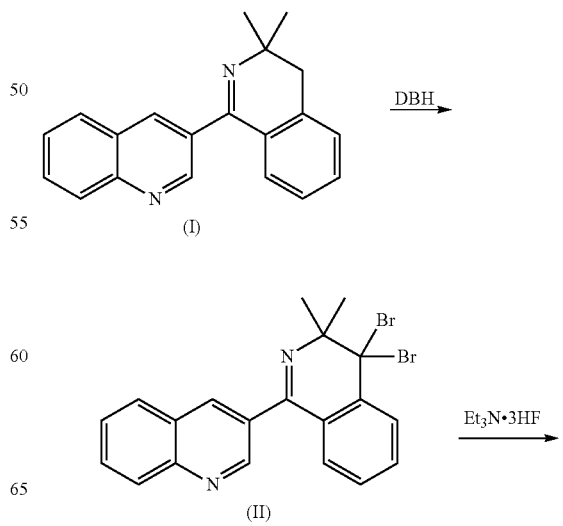

-continued

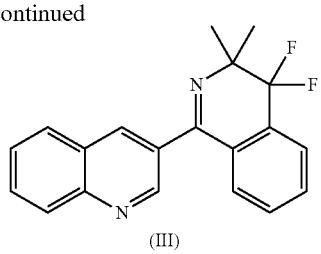

(III)

26.0 g of DBH and 650.2 mg of di(4-tert-butylcyclohexyl) peroxydicarbonate (purity: 93%) were added to 483.87 g of a chlorobenzene solution containing 21.73 g of Compound (I) followed by heating to 65° C. After stirring for 2.5 hours at 65° C., the reaction mixture was cooled to 45° C. and a portion of the chlorobenzene was distilled off under reduced pressure. 213.7 g of the resulting reaction mixture was filtered to obtain 223.4 g of filtrate. The chlorobenzene was further distilled off under reduced pressure to obtain 82.91 g of a chlorobenzene solution of Compound (II) (37.97% by weight, yield: 93.4%).

5.10 g of triethylamine trihydrofluoride were added to 82.77 g of the chlorobenzene solution of Compound (II) obtained by the aforementioned reaction followed by heating to 85° C. and stirring for 6 hours. After cooling to 60° C., 170.0 g of 20% aqueous potassium hydroxide solution were added followed by cooling to room temperature and stirring for 15 minutes. A liquid separation procedure was then carried out to obtain 90.05 g of an organic layer. As a result of analyzing the organic layer by HPLC, Compound (III) was confirmed to have been formed in a yield of 93.4%. The reaction liquid was concentrated under reduced pressure to obtain 35.21 g of a black solution. 189.11 g of ethanol and 12.94 g of concentrated hydrochloric acid were added to the resulting solution followed by heating to 75° C. and stirring for 30 minutes. The solution was then cooled to 2° C. and stirred for 3 hours followed by filtering out the precipitate. 21.85 g of the resulting pale yellow solid were a hydrochloride of Compound (III). Purity: 97.4%, Yield: 84%.

Material Data of Hydrochloride of Compound (III):

$^1$H-NMR (DMSO-D$_6$) δ: 9.32 (1H, d, J=1.8 Hz), 9.04 (1H, d, J=1.8 Hz), 8.31 (2H, dd, J=8.3, 1.8 Hz), 8.06 (1H, dt, J=10.7, 3.9 Hz), 7.93 (1H, d, J=7.6 Hz), 7.88-7.82 (2H, m), 7.75 (1H, t, J=7.5 Hz), 7.57 (1H, d, J=7.6 Hz), 1.40 (6H, s).

Melting point: 188° C. to 191° C.

Elementary Analysis: C, 66.8%; H, 5.0%; N, 7.8%; Cl, 10%; F, 11%

105.0 g of methyl t-butyl ether were added to 28.00 g of a 10% aqueous sodium hydroxide solution followed by adding 21.00 g of the aforementioned hydrochloride of Compound (III) while stirring. After stirring for 30 minutes at room temperature, the liquids were separated and the resulting organic layer was washed with 40 g of water. 27.00 g of ethanol were added to the resulting organic layer followed by heating to 59° C. and distilling off the methyl t-butyl ether. After cooling the solution to 10° C., 84.0 g of water were added followed by stirring for 1 hour at room temperature. The precipitated solid was filtered and dried to obtain 18.79 g of Compound (III) as a pale yellow solid (purity: 98.1%).

Example 11

Synthesis of 6-bromo-3-(4,4-dibromo-3,3-dimethyl-3,4-dihydroisoquinolin-1-yl)quinoline

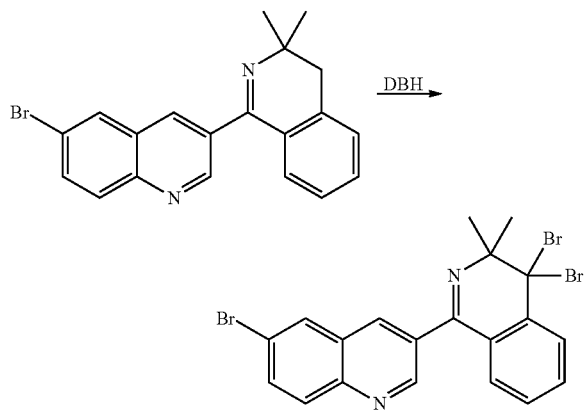

36.98 g of 6-bromo-3-(3,3-dimethyl-3,4-dihydroisoquinolin-1-yl)quinoline were dissolved in 740 ml of chlorobenzene followed by the addition of 34.74 g of DBH and 4.33 g of di(4-tert-butylcyclohexyl) peroxydicarbonate (purity: 93%) and heating to 80° C. After stirring for 4 hours at 80° C., the reaction liquid was cooled to 18° C. and then filtered. After distilling the filtrate under reduced pressure to remove the solvent, 168 g of chloroform were added to the residue followed by heating to 60° C. and stirring for 10 minutes at the same temperature. After cooling to 20° C. the reaction mixture was allowed to stand without stirring for 2 hours at the same temperature. The precipitate was then filtered out to obtain 36.03 g of the title compound as a solid. Yield: 68%.

Material Data of Title Compound:

$^1$H-NMR (CDCl$_3$) δ: 9.13 (1H, d, J=2.1 Hz), 8.27 (1H, d, J=2.1 Hz), 8.22 (1H, dd, J=7.8, 1.1 Hz), 8.05 (2H, dd, J=3.1, 1.5 Hz), 7.85 (1H, dd, J=9.2, 2.1 Hz), 7.64 (1H, td, J=7.6, 1.2 Hz), 7.43 (1H, td, J=7.6, 1.2 Hz), 7.21 (1H, dd, J=7.6, 0.9 Hz), 1.65 (6H, brs).

Example 12

Synthesis of 6-bromo-3-(4,4-difluoro-3,3-dimethyl-3,4-dihydroisoquinolin-1-yl)quinoline

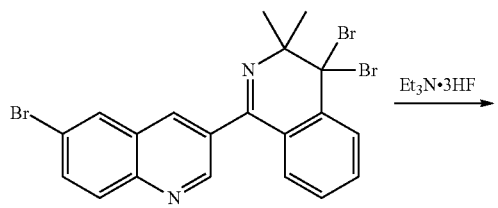

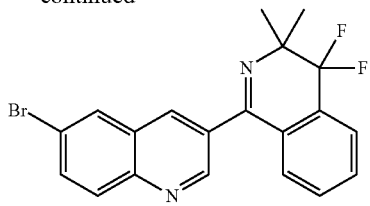

35.93 g of 6-bromo-3-(4,4-dibromo-3,3-dimethyl-3,4-dihydroisoquinolin-1-yl)quinoline were dissolved in 216 ml of toluene followed by the addition of 36.54 g of triethylamine trihydrofluoride, heating to 85° C. and stirring for 4 hours at the same temperature. After cooling to 30° C., 248.0 g of 20% aqueous potassium hydroxide solution were added followed by stirring for 30 minutes. An organic layer obtained by carrying out a liquid separation procedure was washed with water and the organic layer was dried with sodium sulfate. After filtering out the sodium sulfate, the filtrate was concentrated under reduced pressure to obtain 27.10 g of a brown oil. 62.90 g of ethanol were added to the resulting brown oil followed by heating to 70° C. and stirring for 10 minutes. After cooling the solution to 2° C. and stirring for 2 hours, the precipitate was filtered out. 22.31 g of the resulting white solid were the title compound. Yield: 81%.

Material Data of Title Compound:
$^1$H-NMR (CDCl$_3$) δ: 9.15 (1H, d, J=2.1 Hz), 8.30 (1H, d, J=2.1 Hz), 8.05-8.04 (2H, m), 7.88 (1H, d, J=7.6 Hz), 7.85 (1H, dd, J=9.2, 2.1 Hz), 7.67 (1H, td, J=7.5, 1.0 Hz), 7.55 (1H, t, J=7.6 Hz), 7.30 (1H, dd, J=7.8, 0.8 Hz), 1.46 (6H, s).

Example 13

Synthesis of 7-bromo-3-(4,4-difluoro)-3,3-dimethyl-3,4-dihydroisoquinolin-1-yl)quinoline

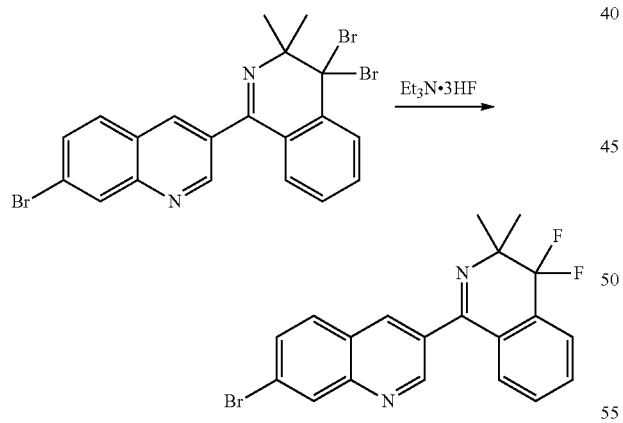

55.7 mg of 7-bromo-3-(4,4-dibromo-3,3-dimethyl-3,4-dihydroisoquinolin-1-yl)quinoline, prepared in the same manner as in Example 11 with the exception of using 7-bromo-3-(3,3-dimethyl-3,4-dihydroisoquinolin-1-yl)quinoline instead of 6-bromo-3-(3,3-dimethyl-3,4-dihydroisoquinolin-1-yl)quinoline, were dissolved in 0.33 ml of toluene followed by the addition of 60 mg of triethylamine trihydrofluoride. The reaction mixture was heated to 95° C. and stirred for 4 hours at the same temperature. After cooling to 25° C., 6.0 g of 10% aqueous potassium hydroxide solution were added followed by stirring for 1 hour. After adding 6 ml of toluene, the liquids were separated and the resulting organic layer was washed with 6 g of water followed by drying the organic layer with sodium sulfate. After filtering out the sodium sulfate, the filtrate was concentrated under reduced pressure and the resulting residue was purified by silica gel column chromatography. 26.4 mg of the resulting white solid were the title compound. Yield: 62%.

Material Data of Title Compound:
$^1$H-NMR (CDCl$_3$) δ: 9.14 (1H, d, J=2.1 Hz), 8.38-8.36 (2H, m), 7.88 (1H, d, J=7.6 Hz), 7.76 (1H, d, J=8.6 Hz), 7.71-7.65 (2H, m), 7.55 (1H, t, J=7.6 Hz), 7.31 (1H, dd, J=7.6, 0.6 Hz), 1.45 (6H, s).

Example 14

Synthesis of 3-(4,4-dibromo-3,3-dimethyl-3,4-dihydroisoquinolin-1-yl)-7-fluoroquinoline

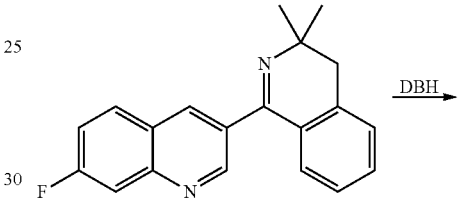

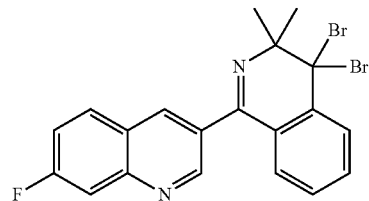

Material Data of Title Compound:
$^1$H-NMR (CDCl$_3$) δ: 9.12 (1H, d, J=2.1 Hz), 8.37 (1H, d, J=2.1 Hz), 8.22 (1H, dd, J=8.0, 1.2 Hz), 7.89 (1H, dd, J=8.9, 6.1 Hz), 7.81 (1H, dd, J=10.1, 2.4 Hz), 7.63 (1H, td, J=7.6, 1.2 Hz), 7.45-7.39 (2H, m), 7.23 (1H, dd, J=7.6, 1.2 Hz), 1.68 (6H, br s).

Example 15

Synthesis of 3-(4,4-difluoro-3,3-dimethyl-3,4-dihydroisoquinolin-1-yl)-7-fluoroquinoline

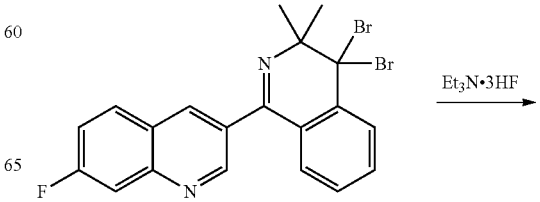

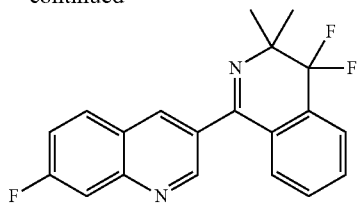

101.0 mg of 3-(4,4-dibromo-3,3-dimethyl-3,4-dihydroisoquinolin-1-yl)-7-fluoroquinoline were dissolved in 0.6 ml of toluene followed by the addition of 60 mg of triethylamine trihydrofluoride. The mixture was heated to 90° C. and stirred for 4 hours at the same temperature. After cooling to 25° C., 6.0 g of 10% aqueous potassium hydroxide solution were added followed by stirring for 1 hour. After adding 6 ml of toluene, an organic layer obtained by carrying out a liquid separation procedure was washed with 6 g of water and the organic layer was dried with sodium sulfate. After filtering out the sodium sulfate, the filtrate was concentrated under reduced pressure and the resulting residue was purified by silica gel column chromatography. 57.1 mg of the resulting colorless oil were the title compound. Yield: 77%.

Material Data of Title Compound:
$^1$H-NMR (CDCl$_3$) δ: 9.15 (1H, d, J=2.1 Hz), 8.40 (1H, d, J=2.1 Hz), 7.91-7.87 (2H, m), 7.81 (1H, dd, J=9.8, 2.4 Hz), 7.67 (1H, t, J=7.5 Hz), 7.55 (1H, t, J=7.6 Hz), 7.41 (1H, td, J=8.6, 2.7 Hz), 7.33 (1H, d, J=7.6 Hz), 1.46 (6H, s).

Example 16

Synthesis of 3-(4,4-dibromo-3-chloromethyl-3-methyl-3,4-dihydroisoquinolin-1-yl)quinoline

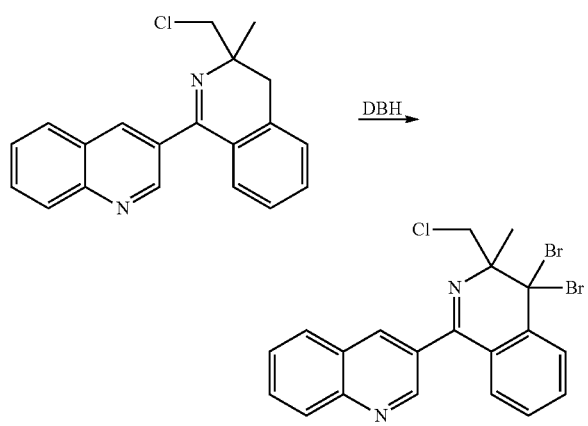

651.0 mg of 3-(3-chloromethyl-3-methyl-3,4-dihydroisoquinolin-1-yl)quinoline were dissolved in 13.35 g of chlorobenzene followed by the addition of 696.2 mg of DBH and 87.0 mg of di(4-tert-butylcyclohexyl) peroxydicarbonate (purity: 93%) and heating to 65° C. After stirring for 5 hours at 65° C., the reaction liquid was cooled to 25° C. and then filtered. After distilling the filtrate to remove the solvent, the residue was purified by silica gel column chromatography. 461.4 mg of the resulting solid were the title compound. Yield: 48%.

Material Data of Title Compound:
$^1$H-NMR (CDCl$_3$) δ: 9.16 (1H, d, J=2.1 Hz), 8.43 (1H, d, J=2.1 Hz), 8.20 (2H, t, J=9.2 Hz), 7.91 (1H, dd, J=8.3, 1.2 Hz), 7.82 (1H, m), 7.66 (1H, td, J=7.6, 1.2 Hz), 7.62 (1H, m), 7.47 (1H, td, J=7.6, 1.2 Hz), 7.32 (1H, dd, J=7.6, 0.9 Hz), 4.42 (2H, br s), 1.43 (3H, br s).

Example 17

Synthesis of 3-(3-chloromethyl-4,4-difluoro-3-methyl-3,4-dihydroisoquinolin-1-yl)quinoline

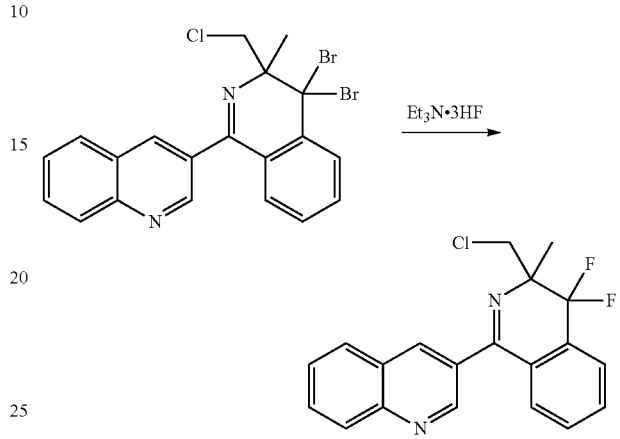

461.4 mg of 3-(4,4-dibromo-3-chloromethyl-3-methyl-3,4-dihydroisoquinolin-1-yl)quinoline were dissolved in 3 ml of toluene followed by the addition of 520 mg of triethylamine trihydrofluoride. The mixture was then heated to 90° C. and stirred for 6 hours at the same temperature. After cooling to 25° C., 7.0 g of 20% aqueous potassium hydroxide solution were added and stirred for 30 minutes. After adding ethyl acetate, an organic layer obtained by carrying out a liquid separation procedure was dried with sodium sulfate. After filtering out the sodium sulfate, the filtrate was concentrated under reduced pressure and the resulting residue was purified by silica gel column chromatography. 332.2 mg of the resulting solid were the title compound. Yield: 97%.

Material Data of Title Compound:
$^1$H-NMR (CDCl$_3$) δ: 9.17 (1H, d, J=2.1 Hz), 8.43 (1H, d, J=2.1 Hz), 8.19 (1H, d, J=8.6 Hz), 7.90 (2H, t, J=8.6 Hz), 7.82 (1H, m), 7.69 (1H, td, J=7.6, 0.9 Hz), 7.62 (1H, m), 7.58 (1H, t, J=7.6 Hz), 7.47 (1H, dd, J=7.6, 0.9 Hz), 3.99 (2H, s), 1.48 (3H, s).

INDUSTRIAL APPLICABILITY

According to the present invention, a 4,4-difluoro-3,4-dihydroisoquinoline derivative can be provided both easily and efficiently. Moreover, the present invention has high value in terms of industrial use since it enables industrial production to be carried out advantageously.

The invention claimed is:
1. A method for producing a compound represented by general formula (1):

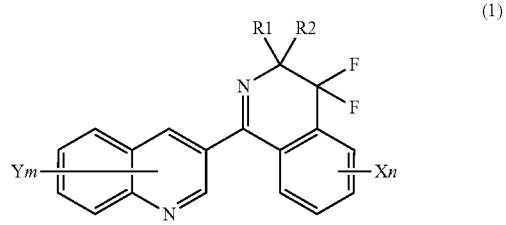

wherein R1 and R2 independently represent an unsubstituted or substituted alkyl group having 1 to 6 carbon atoms or R1 and R2 together with the carbon atom to which they are bound form an unsubstituted or substituted cycloalkyl group having 3 to 10 carbon atoms, X represents a halogen atom, unsubstituted or substituted alkyl group having 1 to 6 carbon atoms or unsubstituted or substituted alkoxy group having 1 to 6 carbon atoms, n represents an integer of 0 to 4, Y represents a halogen atom, unsubstituted or substituted alkyl group having 1 to 6 carbon atoms or unsubstituted or substituted alkoxy group having 1 to 6 carbon atoms, and m represents an integer of 0 to 6, comprising reacting a compound represented by general formula (2):

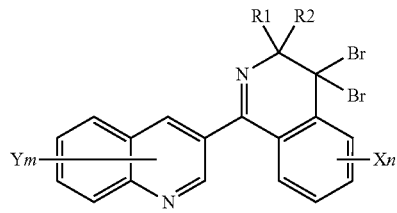

(2)

wherein R1, R2, X, Y, n and m are the same as previously defined, with hydrogen fluoride.

2. The method for producing a compound represented by general formula (1) described in claim 1, wherein the compound represented by general formula (2) is obtained by reacting a compound represented by general formula (3):

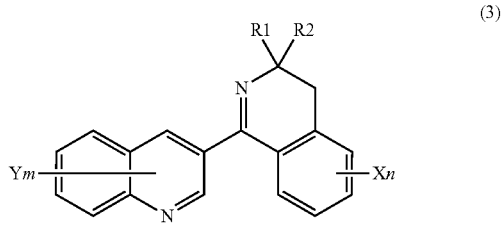

(3)

wherein R1, R2, X, Y, n and m are the same as in claim 1, with a brominating agent.

3. The method for producing a compound represented by general formula (1) described in claim 1, wherein R1 and R2 independently represent an unsubstituted or substituted alkyl group having 1 to 6 carbon atoms, n=0 and m=0.

4. The method for producing a compound represented by general formula (1) described in claim 2, wherein R1 and R2 independently represent an unsubstituted or substituted alkyl group having 1 to 6 carbon atoms, n=0 and m=0.

\* \* \* \* \*